United States Patent

Grossi

[11] Patent Number: 6,053,861
[45] Date of Patent: Apr. 25, 2000

[54] SELF-CLOSING SEAL FOR A MEDICAL INSTRUMENT

[75] Inventor: Bendetto Grossi, Stamford, Conn.

[73] Assignee: Circon Corporation, Santa Barbara, Calif.

[21] Appl. No.: 09/075,989

[22] Filed: May 11, 1998

[51] Int. Cl.[7] .................................................. A61B 1/00
[52] U.S. Cl. .......................................... 600/154; 604/167
[58] Field of Search ............................ 604/167; 600/104, 600/154, 159

[56] References Cited

U.S. PATENT DOCUMENTS

| | | | |
|---|---|---|---|
| 4,198,959 | 4/1980 | Otani | 600/106 |
| 4,240,411 | 12/1980 | Hosono | 600/154 |
| 4,649,904 | 3/1987 | Krauter et al. | 600/154 |
| 4,809,679 | 3/1989 | Shimonaka et al. | |
| 5,342,316 | 8/1994 | Wallace | 604/167 |
| 5,443,452 | 8/1995 | Hart et al. | 604/167 |
| 5,456,284 | 10/1995 | Ryan et al. | 600/159 |
| 5,613,956 | 3/1997 | Patterson et al. | |
| 5,628,732 | 5/1997 | Antoon, Jr. et al. | 604/167 |
| 5,743,883 | 4/1998 | Visconti | 604/169 |
| 5,820,600 | 10/1998 | Carlson et al. | 604/167 |

Primary Examiner—Linda C. M. Dvorak
Assistant Examiner—Brad C. Blaise
Attorney, Agent, or Firm—Bradley M. Ganz

[57] ABSTRACT

A seal for the accessory port of a medical instrument comprises a first region having an aperture formed in elastomeric material. The aperture permits an accessory of slightly greater diameter to be sealably introduced through the accessory port of the instrument. The seal includes a second region of elastomeric material distal to the first region, which includes a hatch with a closeable passageway. The hatch sealably engages the accessory and also seals the accessory port when no accessory is in place. The first region and/or the second can be stretched and distorted as an accessory passes therethrough. Therefore, it is preferable to dispose a relief cavity between the aperture and the hatch. The relief cavity separates the two regions so that the aperture and hatch can each independently maintain an effective seal around an accessory. The relief cavity also provides a break between the aperture and hatch that minimizes drag on the accessory. The seal may include a compression element around the outer surface. Preferably, the compression element is a ring that provides predetermined coaxial compression on the passageway in the hatch through which an accessory is extended.

19 Claims, 3 Drawing Sheets

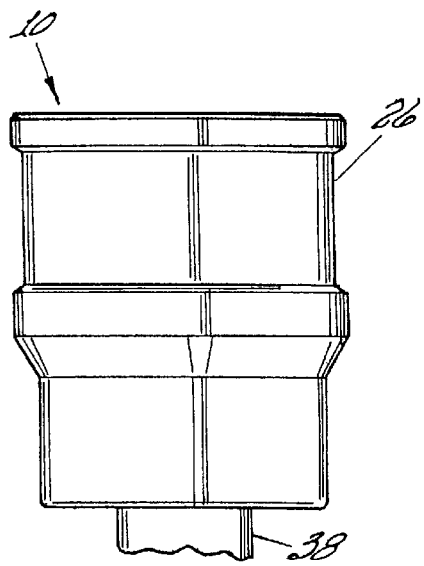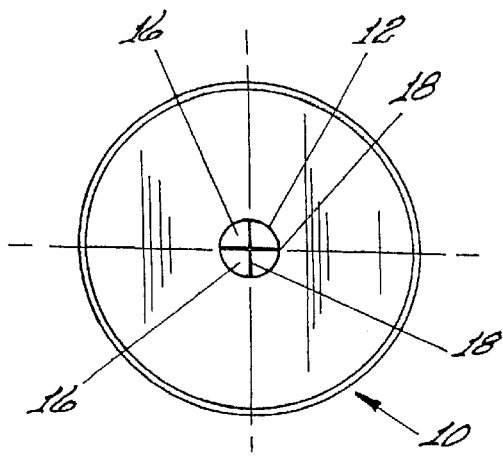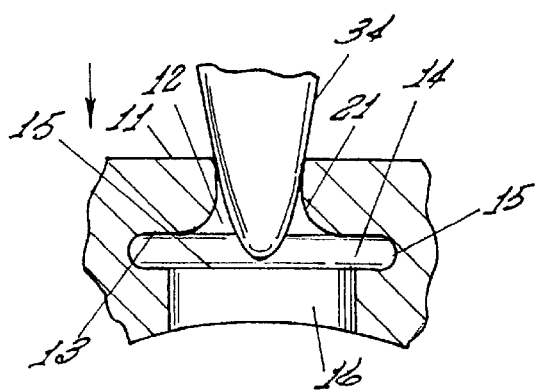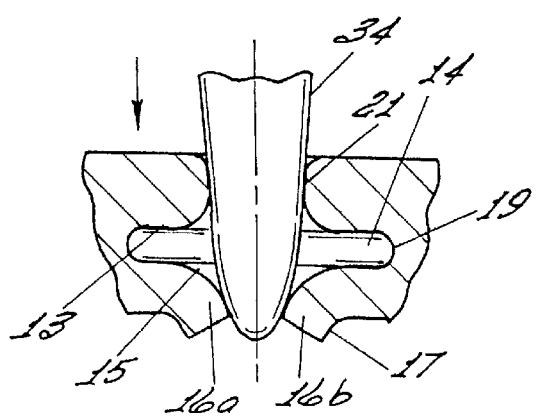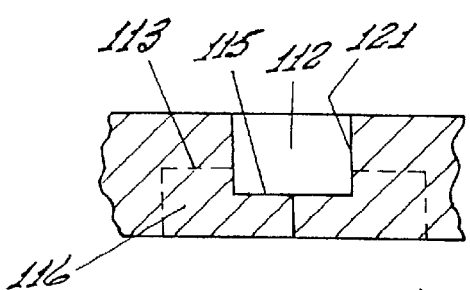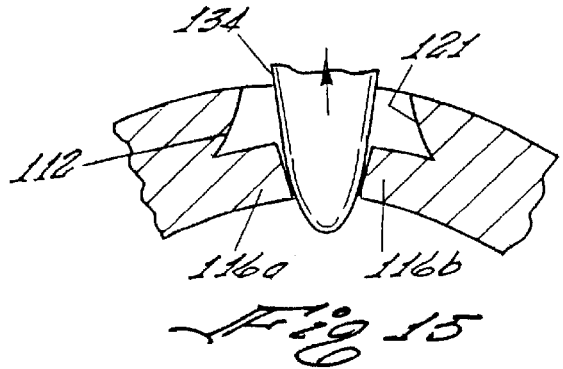

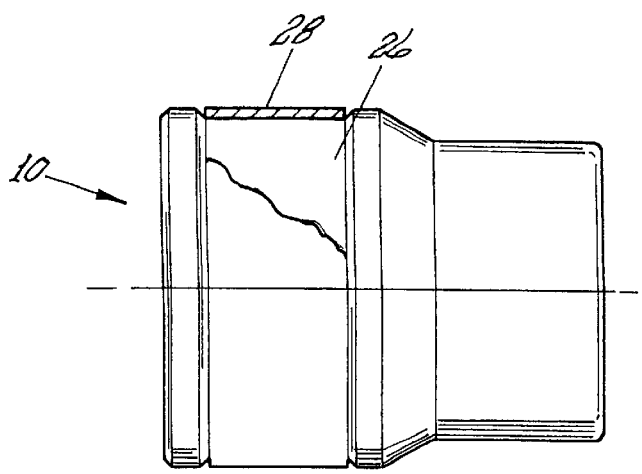
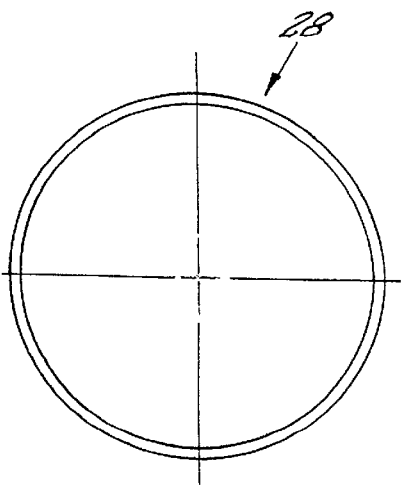
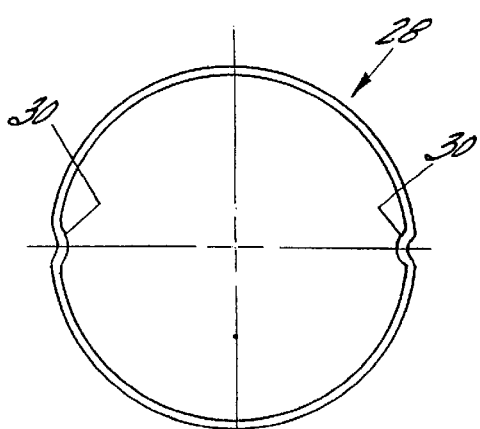
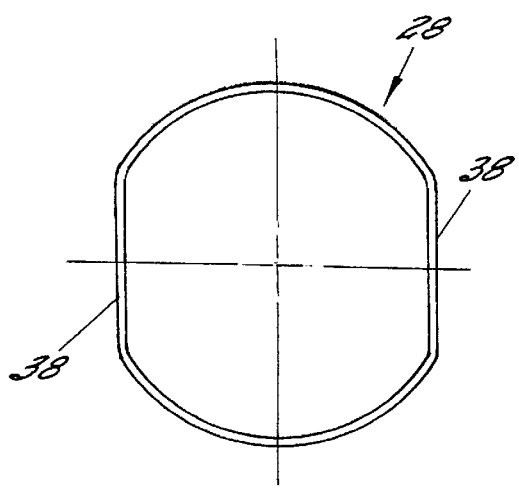
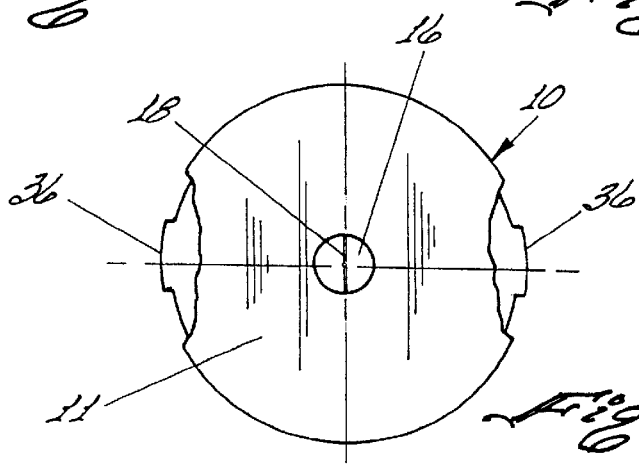

SELF-CLOSING SEAL FOR A MEDICAL INSTRUMENT

BACKGROUND OF THE INVENTION

This invention relates to seals for preventing bodily fluids, irrigation fluids, or distention fluids from escaping from a medical instrument inserted within a patient's body. In particular, the invention relates to elastomeric seals for accessory instrument ports in endoscopic medical instruments.

Endoscopic instruments include accessory ports for introducing other instruments into the body of a patient. For example, a catheter or guide wire may be introduced through such a port into the vascular system of a patient. Endoscopes include a means for providing a seal (1) when no accessory is in the port, (2) as an accessory is introduced into the port, (3) as the accessory is manipulated for its intended purpose, and (4) as the accessory is withdrawn from the port. Without such sealing capabilities, blood and other bodily fluids, as well as introduced fluids, can escape from the port, leaking or spraying medical personnel and equipment with the fluids. These fluids may contain viruses and other biological agents that pose a risk to the personnel or that contaminate equipment.

To address the problem, endoscopes conventionally have included a valve in a location distal to the accessory port. If no accessory is in place, the valve is closed to prevent bodily fluids from escaping from the instrument. If the valve is opened so that an accessory may be inserted through the port, the port includes an elastomeric seal capable of providing an aperture through which the accessory may be passed. To provide an aperture, a slit may be formed through the center of the seal, which expands to receive the accessory, forming a seal between the accessory and the endoscope port.

Prior art devices of this nature are seen in U.S. Pat. No. 4,809,679 to Shimonaka et al. and U.S. Pat. No. 5,613,956 to Patterson et al. The '679 patent describes an elastic plug body with a slit for use in an endoscope. The plug fits into an endoscope frame above a valve also positioned in the frame. The plug or the frame includes projections oriented perpendicular to the slit to urge the slit closed when the plug is fitted in the frame. The '956 patent relates to an expandable aperture aligned with a subjacent, slitted layer of material.

One of the drawbacks of such devices is that between the time an accessory is removed from the endoscope and the accessory-port valve is closed, blood or other bodily fluid can leak or spray from the port because the seal does not effectively self-close. This happens because the seal around the accessory may be distorted by an accessory passing through and stretching the aperture. In the case of the '956 patent, this has to do with the aperture being directly adjacent to the slitted layer. While it may help to make a seal with a tighter fitting aperture or gasket, a tighter fit compromises the slideability of the accessory through the port.

For the foregoing reasons, there is a need for an improved seal that not only provides an effective seal around a situated accessory, but also provides a leak-free seal as an accessory is withdrawn or inserted through an accessory port. With such a seal, it would be possible to eliminate the valve from the accessory port. By eliminating the valve, endoscopes could be made that are simpler and less expensive to construct. By eliminating the valve, surgeons could operate endoscopes more easily—ease of use is always an important factor in surgery, particularly in minimally-invasive, endoscopic procedures where precision and delicateness are needed.

Unfortunately, until the present invention, there has not been a seal of simple construction that addresses the foregoing problems and needs.

SUMMARY OF THE INVENTION

To address the drawbacks of the prior art, the present invention provides a seal that prevents or minimizes the leakage of blood and other bodily fluids from an accessory port of a medical instrument when an accessory is positioned in or moved through the port. In so doing, the invention reduces the risks inherent to medical personnel from contact with blood and other bodily fluids, and it reduces the risk of spreading contaminants to nearby medical instruments and equipment. Because the present invention prevents leakage and provides tactility, the valve to the accessory port may be eliminated from the medical instrument. Accordingly, endoscopes may be made that are less complicated and expensive to construct and which are simpler to use than the prior art.

More particularly, the seal tends not to be distorted as an accessory is passed through it. The present invention also allows an accessory to be moved through the seal with relatively little friction, and with good tactility to the surgeon.

The present invention also is of such simple construction that it can be cleaned and re-sterilized by the steam autoclave process and reused, thus adding to the market advantage of the design.

In one embodiment, the present invention comprises an elastomeric seal for the accessory port of a medical instrument. The seal includes a first region having an aperture formed in elastomeric material. The aperture is defined by a bore having a circumferential wall disposed between proximal and distal surfaces of the material. The aperture permits an accessory of slightly greater diameter to be sealably introduced into a central bore of the seal and through the accessory port of a medical instrument. The seal includes a second region of elastomeric material distal to the first region, which includes a hatch with a closeable passageway. The hatch also sealably engages the accessory.

In one embodiment of the invention, the hatch comprises a layer of elastomeric material across the longitudinal bore of the seal. One or more slits in the hatch form one or more flaps. An accessory pushes open the flaps to create a passageway through which the accessory is extended. The flaps sealably engage the accessory.

The first region and/or the second regions of the seal can be stretched and distorted as an accessory passes therethrough. This can disrupt the seal around the accessory by the aperture or hatch, allowing fluid leakage. Therefore, it is preferable to dispose a relief cavity between the aperture and the hatch. The relief cavity separates the two regions so that the aperture and hatch can each independently maintain an effective seal around an accessory. The relief cavity also provides a break between the aperture and hatch that minimizes drag on the accessory.

The seal may include a compression element around the outer surface. Preferably, the compression element is a ring that provides predetermined coaxial compression on the passageway in the hatch through which an accessory is extended. This compression improves the self-closing capabilities of the seal. In the case of a slitted hatch, the compression element helps urge the slits closed for better sealing with or without an accessory in place. The compression element may include rib-like projections that apply pressure at predetermined areas along the exterior surface of the seal. Preferably, the pressure is applied perpendicular to slits in the hatch to urge the opposing surfaces of the slits together. This localized compression improves self-closing capabilities without substantially compromising drag on the various size accessories. An alternative to the embodiment of a ribbed compression element is one where the ribs are instead located on the exterior surface of the sealed body. The outer circumferential surface of the seal may include a recess into which a compression element may be seated. Advantageously, the present invention may also be molded from a single material into a single-piece seal using common molding techniques.

DESCRIPTION OF THE DRAWINGS

FIG. 5 shows the seal of FIG. 4 fitted over a stem-based accessory port, such as a Luer port, of a medical instrument.

FIG. 6 shows the seal of FIG. 2, but in this case the hatch distal the aperture includes multiple slits, providing a passageway for an accessory.

FIG. 7 shows a section of the seal of FIG. 2 taken through the slit in the hatch, and it illustrates an accessory being introduced into the proximal aperture of the seal.

FIG. 8 shows the seal of FIG. 7 taken with the accessory penetrating further into the seal from a 90° view to FIG. 7.

FIG. 9 shows a side view of the seal of FIG. 1 with a compression element shown in partial section view disposed around the seal.

FIG. 10 shows a top view of the compression element of FIG. 9.

FIG. 11 shows a top view of another embodiment of a compression element that includes ribs for providing localized compression on the seal.

FIG. 12 shows a top view of a further embodiment of a compression element that includes flattened areas for providing localized compression on the seal.

FIG. 13 shows a further embodiment of a self-closing seal of the present invention in partial section showing ribs disposed on the exterior surface of the seal so that a compression element of FIG. 10, for example, can engage the ribs to provide localized compression on the seal.

FIG. 14 shows a partial view of a seal, not of the present invention, without a relief cavity separating the aperture and hatch of the seal.

FIG. 15 shows the seal and accessory of FIG. 14 as the accessory is withdrawn from the seal aperture and hatch to indicate how the absence of the relief cavity results in distortion of the seal.

DETAILED DESCRIPTION

Figure 1:
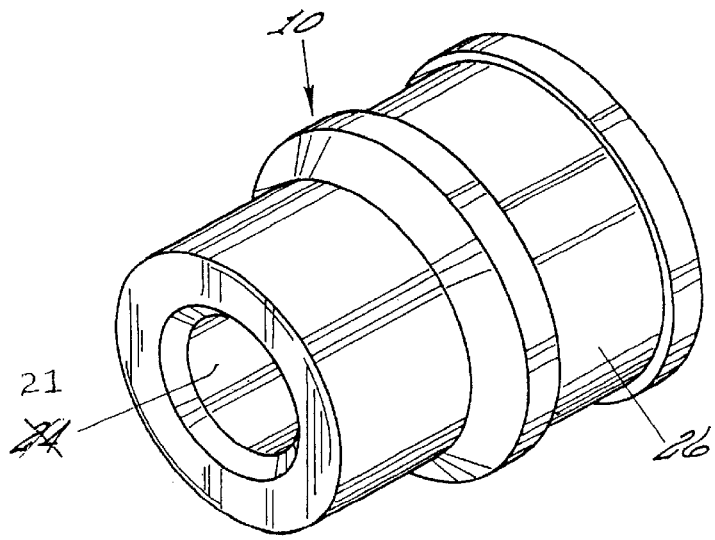
FIG. 1 provides a perspective view of a self-closing seal of the present invention.

It is to be understood that while this invention is generally described in terms of endoscopes, the invention also pertains to other medical instruments that have a port for intracorporeal insertions of accessories. Accessories that may be inserted through the port of an endoscope include catheters, guidewires, forceps, scissors, electrosurgical probes, stone baskets, retrievers, and other accessories and probes.

FIGS. 1–4 show one example of a seal according to the present invention. Seal 10 includes passageway 12 at its proximal end. The passageway 12 may be an aperture as shown in the figures. Alternatively, it may be any other means for sealably engaging an accessory, such as one or more slits in an elastomeric material. The use of an elastomeric material is preferably so that a range of sizes may be accommodated.

The aperture 12 is formed in medical grade elastomeric material having a proximal surface 11 and a distal surface 13. The aperture is defined by circumferential wall 21 that separates proximal surface 11 from distal surface 13. The material should have a durometer that minimizes drag around the accessory and simultaneously holds an accessory in position. It should also seal well and be capable of expanding to hold a range of accessory sizes. In the case of most elastomers, the range should be about 20 Shore A Durometer to about 40 Shore. In one embodiment suitable for a range of sizes, silicone rubber is molded to form a one-piece seal of about 40 Shore A Durometer. Persons skilled in the art will recognize that various other materials or durometers, alone or in combination, may also meet the aforementioned functional requirements.

The diameter of aperture 12 is such that an accessory introduced into the aperture engages the walls of the aperture in a snug to tight manner to form a seal around the accessory as it is inserted into the device. By using an elastomeric material, the aperture expands to accept a range of accessory sizes. The seal should not be so tight that it is difficult to slide an accessory through the seal.

Figures 2, 3:
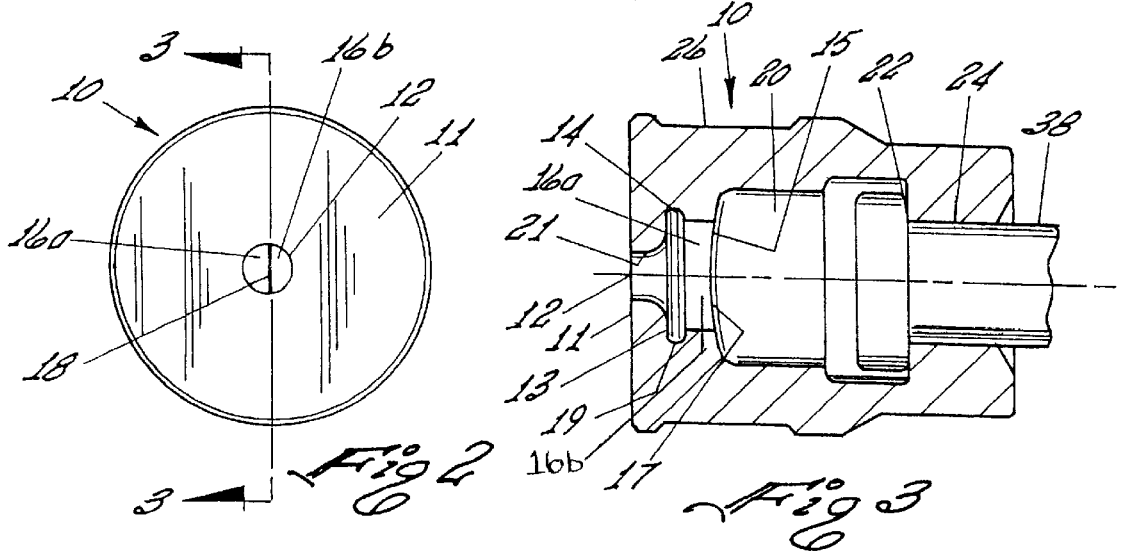
FIG. 2 shows a top view of the proximal end of a self-closing seal of the present invention, including a view of a single slit disposed in a hatch, providing a passageway for an accessory.
FIG. 3 is a cross-sectional view of the seal of FIG. 2 taken along line 3—3, as well as the stem of a Luer port seated in the recess of the seal.
Figure 4:
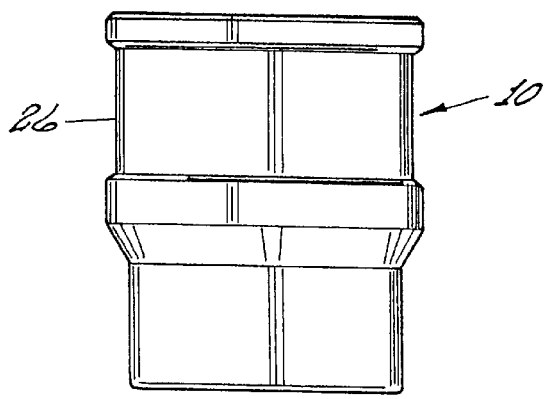
FIG. 4 shows a side view of the seal shown in FIG. 1.

Seal 10 includes a self-closing distal passageway 16. In the embodiments shown in the Figures, passageway 16 comprises a hatch. The hatch 16 provides a closeable passageway across the central bore of the seal. The hatch has top surface 15 and bottom surface 17. An annular relief cavity 14 is located between aperture 12 and hatch 16, and is discussed in detail below. Hatch 16 may include one slit 18 that defines displaceable flaps 16(a) and 16(b). Or, it could include multiple slits, which would result in multiple flaps. FIG. 2 shows a seal 10 having a single slit 18 across the center of hatch 16. FIG. 6 shows a hatch with multiple slits 18. The slits 18 allow accessory 34 to pass through the central bore of the seal while maintaining a seal around the accessory as it moves through the passageway of the hatch, as shown in FIGS. 7 and 8. The slits are resilient and self-close upon removal of the accessory.

To provide sealability and resilience, hatch 16 is preferably made of an elastomeric material. Like aperture 12, hatch 16 can expand to sealably engage the accessory as it is passed through or positioned in seal 10. Hatch 16 is also intended to self-close when an accessory is not in place. The hatch may be made of the same or similar material in which the aperture is formed. The elastomeric construction of hatch 16 allows opposing sections of hatch 16 to self-closeably urge against each other to form a seal when no accessory is positioned or being moved through seal 10. The seal of hatch 16 against an accessory should not be so tight as to affect the slideability of the accessory.

Seal 10, as shown in FIG. 3, also includes an intermediate cavity 20. Intermediate cavity 20 provides a space for the flaps 16(a) and 16(b) of hatch 16 to be displaced into when an accessory is passed therethrough. Cavity 20 also provides a reservoir for fluid that enters the seal. The accessory pushes back flaps 16(a) and (b) in the process.

Referring to FIG. 8, it can be seen that relief cavity 14 establishes a space between aperture 12's distal surface 13, and hatch 16's proximal surface 15. Relief cavity 14 serves to isolate the sealing elements of the seal—aperture 12 and hatch 16—from the distortion caused by drag of the accessory on the seal. The relief cavity 14 thereby enables aperture 12 and hatch 16 to form seals independently around accessory 34 as the accessory is positioned in seal 10 or as it moves in or out of it. Relief cavity 14 includes radial wall 19, which expands radially wider than the lower opening of aperture 12 in distal surface 13, leading into relief cavity 14. Without relief cavity 14, the proximal surface of hatch 16 would sit flush against the distal surface 13 defining aperture 12 and such independent sealing would be impeded. Generally for existing medical endoscope accessories of 2–12 French size, a suitable separation of the proximal hatch surface 16 from distal surface 13 is about 0.02 to about 0.1 inches.

Referring to FIGS. 14 and 15, if surface 115 of hatch 116 were to sit flush against surface 113 of aperture 112, accessory 134's drag against inner surfaces of the seal would tend to stretch and distort the seal. FIG. 15 shows the seal and accessory of FIG. 14 as accessory 134 is being withdrawn from the seal. It is believed that in the absence of a relief cavity 14, aperture 112 does not effectively seal around the accessory due to the distortion, as illustrated in FIG. 15. Consequently, bodily fluids trailing the accessory through the aperture could leak from aperture 112 as an accessory is withdrawn from it. It is also believed that the distortion may cause the flaps 116a and 116b to sit more tangentially to the accessory, resulting in a less effective seal around the accessory, as illustrated by comparing FIG. 8 with FIG. 15. In the present invention, relief cavity 14 separates the hatch 16 from the distal surface 13 of the aperture: any deformation of the seal occurring as the accessory is moved through the aperture or hatch should have little or no effect on the hatch's ability to seal around accessory 34, as shown in FIG. 8.

The present invention teaches the construction of seal that has two separated regions for sealably engaging an accessory, and it will be recognized by persons skilled in the art that proximal passageway 12 and self-closing, distal passageway 16 are examples, not limitations of passageways, that sealably engage an accessory and/or are self-closing. For example, either aperture 12 and/or hatch 16 could be replaced by an intact layer of material that is pierceable by an accessory having a needle or other piercing structure. The piercing structure creates an opening in the layer that sealably engages the accessory. In another variation, the distal and proximal passageways may be formed in or of the same material or different materials of the same or different durometers.

The seal 10 includes port receptacle regions 22 and 24 distal to cavity 20, which define a recess for receiving a standard Luer port stem 38 or barbed stem, for example. As seen in FIG. 3,the receptacle 22 receives the upper flared region of a Luer port stem 38, and receptacle 24 sealably receives the shaft of the Luer port stem. The seal can also be designed to fit over a barbed connector or other stem-like ports, or it may be designed to plug into a port instead of fitting over one.

FIGS. 9–13 show other embodiments of a seal according to the present invention. Turning to FIG. 9, a compression element 28 may be circumferentially disposed around a proximal portion of the seal. Preferably, the compression element is disposed in a compression element recess 26. FIGS. 10–12 show other examples of a compression element 28. FIG. 10 shows the compression element as a ring. In FIG. 11, the compression element is a ring that includes one or more ribs 30. The ribs provide localized compression on hatch 16 to urge flaps 16a and b around accessory 34 for improved sealing capabilities without significantly affecting drag on a range of accessory sizes. The ribs also provide improved self-closing capability when the accessory is removed. Preferably, opposing ribs 30 should be oriented parallel to a slit 18 or slits 18 to deliver a perpendicular force to the slit or slits.

A variation of this concept demonstrating this principle is shown in FIG. 13. In this embodiment, one or more opposing ribs 36 are contained on the outer surface of recess 26 in substantial alignment with hatch 16. A compression element such as the standard ring of FIG. 10 acts on the ribs to provide the localized compression. The ribs are located on opposite sides of slit 18 to urge the opposing sections of hatch 16 together. FIG. 12 shows compression element 28 that has two flattened areas 38 instead of ribs. This embodiment will provide localized compression in the same manner as the ribs do. In the foregoing embodiments, the ring can be preformed into a particular shape. Alternatively, that shape can be preformed or flattened after it is assembled onto a molded seal. Rings should be made of a material that satisfies known medical requirements, such as sterilizability. In terms of functionality, suitable ring materials include metals, ceramic, Liquid Crystal Polymer (LCP), polysulphone, polyethersulphone, polycarbonate, polyimide. These materials may be added onto the seal at assembly or molded integrally with the seal. It may be advantageous to use a shrinkable material that is added at assembly.

Some suitable shrinkable materials include polyvinylidene fluoride, and polyester.

One example of a self-closing seal, in accordance with FIGS. 2 and 3, suitable for a 2–7 French range of accessory sizes, has an outer diameter of about 0.46"; an aperture 12 of about 0.02" diameter and of about 0.04" depth; a relief cavity 14 of about 0.13" diameter and about 0.02" depth; an intermediate cavity 20 of about 0.260" diameter and of about 0.16" depth; and a slit 18 of about 0.04" thickness and of about 0.09" length.

Another example of a self-closing seal, in accordance with FIGS. 2 and 3, suitable for a 6–12 French range of accessory sizes, has an outer about 0.46" ; an aperture 12 of about 0.07" diameter and of about 0.04" depth; a relief cavity 14 of about 0.2" diameter and about 0.02" depth; an intermediate cavity 20 of about 0.26" diameter and of about 0.16" depth; and a slit 18 of about 0.04" thickness and of about 0.16" length.

With respect to both examples, silicone rubber of 40±5 Shore A Durometer may be molded into a seal of the foregoing dimensions.

The invention having been described, it will be readily apparent that many other variations are possible. Such variations are not to be regarded as a departure from the spirit and scope of the invention, and all such variations are intended to be included within the scope of the following claims.

What is claimed:

1. A seal for the accessory port of a medical instrument comprising:
   a first proximal region having an aperture for sealably engaging an accessory of at least slightly greater diameter, the aperture being formed in an elastomeric material having proximal and distal surfaces and defined by a circumferential wall;
   a second region of elastomeric material distal to the first region having a hatch disposed across the central bore of the seal, the hatch being a closeable passageway with a top surface through which the accessory may be sealably extended, a compression element being disposed around the exterior surface of the second region of the seal; and a third region comprising a relief cavity that separates the distal aperture surface from the top surface of the hatch.

2. The seal of claim 1 further comprising a fourth region distal to the second region and adapted to sealably connect to the accessory port of the medical instrument.

3. The seal of claim 2 wherein the fourth region is adapted to connect to a Luer port on a medical instrument.

4. The seal of claim 2 wherein the seal is formed from a single molded piece of material.

5. The seal of claim 1 wherein the compression element includes one or more pressure ribs oriented to urge the hatch into a sealed position.

6. The seal of claim 1 wherein the exterior of the seal includes one or more pressure ridges engageable with a compression element and oriented to urge hatch into a sealed position.

7. The seal of claim 1 wherein the closeable passageway comprises at least one slit to enable an accessory to sealably extend through the hatch.

8. The seal of claim 1 wherein the hatch comprises a layer of elastomeric material with one or more slits forming two or more flaps through which an accessory may be sealably extended, and one or more sets of opposing ribs are disposed on the exterior surface of the second region of the seal in parallel relation to a slit to urge the slit into a sealed position.

9. A seal for the accessory port of a medical instrument comprising:

a first proximal region having an aperture for sealably engaging an accessory of at least slightly greater diameter, the aperture being formed in an elastomeric material having proximal and distal surfaces and defined by a circumferential wall;

a second region of elastomeric material distal to the first region having a hatch disposed across the central bore of the seal, the hatch including a closeable passageway with a top surface through which the accessory may be sealably extended wherein a compression element fits around a recess in the exterior surface of the second region to maintain the passageway in the hatch sealably engaged against an accessory to minimize leakage of bodily fluid therethrough during an endoscopic procedure; and a third region comprising a relief cavity that separates the distal aperture surface from the top surface of the hatch.

10. The seal of claim 9 wherein the compression element comprises a substantially ring-shaped element.

11. A seal for the accessory port of a medical instrument comprising:

a first proximal region having an aperture for sealably engaging an accessory of at least slightly greater diameter, the aperture being formed in an elastomeric material having proximal and distal surfaces and defined by a circumferential wall;

a second region of elastomeric material distal to the first region having a hatch disposed across the central bore of the seal, the hatch being a closeable passageway with a top surface through which the accessory may be sealably extended, a compression element being disposed around the exterior surface of the second region of the seal;

a third region comprising a relief cavity that separates the distal aperture surface from the top surface of the hatch;

a fourth region distal to the second region and adapted to sealably connect to the accessory port of a medical instrument; and the first, second, and third regions being molded to form a single piece.

12. The seal of claim 11 wherein the first, second, third, and fourth regions are molded to form a single piece.

13. The seal of claim 12 wherein all regions of the seal are molded to form a single piece seal of a single elastomeric material.

14. The seal of claim 11 wherein the first and second regions have a durometer of about 35 to 45 Shore A.

15. An endoscope having an accessory port, the accessory port including a self-closing seal comprising:

a first proximal region having an aperture for sealably engaging an accessory of at least slightly greater diameter, the aperture being formed in an elastomeric material having proximal and distal surfaces and defined by a circumferential wall;

a second region of elastomeric material distal to the first region having a hatch disposed across the central bore of the seal, the hatch being a closeable passageway with a top surface through which the accessory may be sealably extended, the second region having a recess for receiving a compression element; and a third region comprising a relief cavity that separates the distal aperture surface from the top surface of the hatch.

16. An endoscope having an accessory port, the accessory port including a self-closing seal comprising:

a first proximal region having an aperture for sealably engaging an accessory of at least slightly greater diameter, the aperture being formed in an elastomeric material having proximal and distal surfaces and defined by a circumferential wall;

a second region of elastomeric material distal to the first region having a hatch disposed across the central bore of the seal, the hatch being a closeable passageway with a top surface through which the accessory may be sealably extended, a compression element being disposed around the exterior surface of the second region of the seal;

a third region comprising a relief cavity that separates the distal aperture surface from the top surface of the hatch;

a fourth region distal to the second region and adapted to sealably connect to the accessory port of the medical instrument; and the first, second, and third regions being molded to form a single piece.

17. A seal for the accessory port of a medical instrument comprising:

a first proximal region having an aperture for sealably engaging an accessory of at least slightly greater diameter, the aperture being formed in an elastomeric material having proximal and distal surfaces and defined by a circumferential wall;

a second region of elastomeric material distal to the first region having a hatch disposed across the central bore of the seal, the hatch being a closeable passageway with a top surface through which the accessory may be sealably extended, a compression element being disposed around the exterior surface of the second region of the seal;

a third region comprising a relief cavity that separates the distal aperture surface from the top surface of the hatch;

a fourth region distal to the second region and adapted to sealably connect to the accessory port of the medical instrument; and wherein the separation of the distal surface of the aperture from the top surface of the hatch surface is about 0.02 to about 0.1 inches so that any deformation of the seal occurring as the accessory is moved through the aperture or hatch should have little or no effect on the hatch's ability to seal around the accessory.

18. A seal for the accessory port of a medical instrument comprising:

a first proximal region having an aperture for sealably engaging an accessory of at least slightly greater diameter, the aperture being formed in an elastomeric material having proximal and distal surfaces and defined by a circumferential wall;

a second region of elastomeric material distal to the first region having a hatch disposed across the central bore of the seal, the hatch being a closeable passageway with a top surface through which the accessory may be sealably extended, a compression element being disposed around the exterior surface of the second region of the seal;

a third region comprising a relief cavity that separates the distal aperture surface from the top surface of the hatch; and wherein the aperture and hatch are adapted to sealably engage an accessory of about 2–7 French and the relief cavity separates the distal surface of the aperture from the top surface of the hatch by at least about 0.02 to about 0.05 inches so that any deformation of the seal occurring as the accessory is moved through the aperture or hatch should have little or no effect on the hatch's ability to seal around the accessory.

19. A seal for the accessory port of a medical instrument comprising:

a first proximal region having an aperture for sealably engaging an accessory of at least slightly greater diameter, the aperture being formed in an elastomeric material having proximal and distal surface s and defined by a circumferential wall;

a second region of elastomeric material distal to the first region having a hatch disposed across the central bore of the seal, the hatch being a closeable passageway with a top surface through which the accessory may be sealably extended, a compression element being disposed around the exterior surface of the second region of the seal;

a third region comprising a relief cavity that separates the distal aperture surface from the top surface of the hatch; and wherein the aperture and hatch are adapted to sealably engage an accessory of about 6–12 French and the relief cavity separates the distal surface of the aperture from the top surface of the hatch by at least about 0.02 to about 0.10 inches so that any deformation of the seal occurring as the accessory is moved through the aperture or hatch should have little or no effect on the hatch's ability to seal around the accessory.

* * * * *